US011819304B2

(12) United States Patent
Fliss (10) Patent No.: US 11,819,304 B2
(45) Date of Patent: Nov. 21, 2023

(54) SURGICAL DRAPING DEVICE HAVING A THERMAL FEATURE TO RETAIN NORMAL PATIENT BODY HEAT (71) Applicant: Welmed Inc., Chicago, IL (US)

(72) Inventor: Dave Fliss, Chicago, IL (US)

(73) Assignee: Welmed Inc., Chicago, IL (US)

( * ) Notice: Subject to any disclaimer, the term of this patent is extended or adjusted under 35 U.S.C. 154(b) by 95 days.

(21) Appl. No.: 16/582,747

(22) Filed: Sep. 25, 2019

(65) Prior Publication Data
US 2021/0085414 A1 Mar. 25, 2021

(51) Int. Cl.
A61B 46/20 (2016.01)
A61B 46/00 (2016.01)
A61F 7/03 (2006.01)

(52) U.S. Cl.
CPC ............ A61B 46/40 (2016.02); A61B 46/20 (2016.02); A61F 7/034 (2013.01)

(58) Field of Classification Search
CPC . A61B 46/20; A61B 46/40; A61F 7/03; A61F 7/034
See application file for complete search history.

(56) References Cited

U.S. PATENT DOCUMENTS

| 4,736,088 | A | * | 4/1988 | Bart | A61F 13/00 |
| | | | | | 219/211 |
| 4,807,644 | A | | 2/1989 | Sandhaus | |
| 4,889,135 | A | * | 12/1989 | Poettgen | A61B 46/00 |
| | | | | | 128/849 |
| 5,443,488 | A | | 8/1995 | Namenye et al. | |
| 5,800,483 | A | * | 9/1998 | Vought | A61F 7/00 |
| | | | | | 128/853 |
| 5,857,467 | A | | 1/1999 | Faries, Jr. et al. | |
| 5,991,666 | A | * | 11/1999 | Vought | A61B 46/00 |
| | | | | | 607/104 |
| 6,167,885 | B1 | | 1/2001 | Hanssen | |
| 6,820,622 | B1 | | 11/2004 | Teves et al. | |
| 6,874,505 | B1 | | 4/2005 | Fenwick et al. | |
| 7,096,870 | B2 | | 8/2006 | Lamprich et al. | |
| 7,226,454 | B2 | | 6/2007 | Albrecht et al. | |
| 7,343,919 | B2 | | 3/2008 | Czajka et al. | |
| 7,763,060 | B2 | | 7/2010 | Baumann | |
| 7,819,911 | B2 | | 10/2010 | Anderson et al. | |
| 7,862,599 | B2 | | 1/2011 | Anderson | |

(Continued)

FOREIGN PATENT DOCUMENTS

WO WO 00/67685 * 11/2000

OTHER PUBLICATIONS

Thermal Technology Drapes, viewed Apr. 30, 2019, http://welmed.us/cat/index.php?dispatch=categories.view&category_id=279.

Primary Examiner — Camtu T Nguyen
(74) Attorney, Agent, or Firm — Sean S. Swidler; Swidler Law Group, LLC (57) ABSTRACT A surgical drape for use during pre-operative and post-operative procedures and in sterile operating room environments comprises a drape panel, a heat source affixed to the drape panel for maintaining normal patient body temperature. A thermal panel affixed to the drape panel and defining a heat retention area is optional. The heat source comprises a single or plurality of air-activated chemical warming device for quick heating to optimal temperature and consistent discharge of heat over the desired time.

10 Claims, 8 Drawing Sheets (56) References Cited

U.S. PATENT DOCUMENTS

| | | |
|---|---|---|
| 7,871,428 B2 | 1/2011 | Augustine |
| 7,901,443 B2 | 3/2011 | Vardanega |
| 8,454,672 B2 | 6/2013 | Van Duren |
| 9,642,404 B2 | 5/2017 | Giles et al. |
| 10,235,737 B2 | 3/2019 | Cheatham, III et al. |
| 2008/0053462 A1 | 3/2008 | Teves et al. |
| 2008/0208098 A1* | 8/2008 | Rennix ................. A61F 13/022 602/47 |
| 2010/0198320 A1 | 8/2010 | Pierre et al. |
| 2016/0120691 A1* | 5/2016 | Kirwan .................... A61F 7/02 607/111 |

* cited by examiner

SURGICAL DRAPING DEVICE HAVING A THERMAL FEATURE TO RETAIN NORMAL PATIENT BODY HEAT

FIELD OF THE INVENTION

This invention generally relates to pre-operative, post-operative and operative surgical drapes and particularly relates to a surgical drape providing a thermal feature to help maintain normothermia (patients core temperature) before, during and after the surgical procedure. Additionally by maintaining patient normothermia it will provide an effective barrier to protect a surgical patient from the transfer of microorganisms, body fluids and particulates that might otherwise cause hospital acquired infections (HAI) and potential patient cross-contaminations.

BACKGROUND OF THE INVENTION

During a surgical procedure, there is a need to provide an effective barrier to protect a surgery patient from transfer of microorganisms, body fluids and particulates that might otherwise cause infections. For example, infectious microorganisms may include Methicillin-Resistant *Staphylococcus aureus* (MRSA), which is a bacterium that can lead to skin infections causing redness, swelling, and tenderness of the skin and also possibly causing boils, blisters, pustules, and abscesses on the skin. In addition, a body fluid, such as blood, might contain blood-borne pathogens, such as Human Immunodeficiency Virus (HIV) that can lead to the impairment of the human immune system. Moreover, Hepatitis B and C viruses are also blood-borne pathogens. The Hepatitis B and C viruses can damage the liver. Particulates, on the other hand, may be dried residue from disinfectants or chemicals. The particulates can migrate into the surgical wound and cause infection or the particulate matter can even, at least partially, clog a catheter tube during the surgical procedure.

In order to counter the transfer of microorganisms, body fluids and particulates that might otherwise cause infections, surgical drapes and gowns have been used to protect patients from surgical site infections (SSIs) by preventing or inhibiting microbes from invading the incision created during the surgical procedure. It is known that surgical drapes create a barrier between the surgical field and possible sources of microbes. Also, microbial migration and contamination from nonsterile-to-sterile areas is minimized by isolating the incision site and creating a sterile field with the use of sterile drapes. Finally, surgical drapes protect the patient from their own skin flora (endogenous source of contamination) and the surgical team members and the environment (exogenous sources of contamination).

It is further known that heat loss in a patient during a surgical procedure can lead to serious problems such as hypothermia. Hypothermia can occur when the core body temperature goes below 36° C. (96.8° F.). Hypothermia can then possibly lead to serious complications involving poor circulation of blood, blood coagulation, inadequate wound healing, and slow drug metabolism. Prior to the present invention, as set forth in general terms above and more specifically below, it is known to employ various surgical drapes. See, for example, U.S. Pat. No. 4,936,319 by Neubardt et al., U.S. Pat. No. 5,042,455 by Yue et al., U.S. Pat. No. 7,096,870 by Lamprich et al., U.S. Pat. No. 7,763,060 by Baumann, U.S. Pat. No. 7,879,078 by Vardanega, U.S. Pat. No. 8,097,031 by Anderson et al., U.S. Pat. No. 8,372,129 by Baumann, U.S. Pat. RE34,816 by Poettgen, U.S. Pat. RE35,427 by Poettgen, U.S. Patent Application 2006/0191540 by Lamprich et al., U.S. Patent Application 2011/0077724 by Anderson et al., and U.S. Patent Application 2012/0298117 by Giles et al.

While these surgical drapes can be used to counter the transfer of microorganisms, body fluids and particulates that might otherwise cause infections and reduce the rate of heat loss in the patient, there is nevertheless a need for a new version of a patient heat retention product that is a stand-alone option for surgical drapes.

Standalone refers to the surgical drape providing the heat retention property without the need to be attached to an electrical, fluid or warm air driven source of heat retention. Thermal panel(s) are incorporated into the surgical drapes, as well as into the pre and post-operative surgical drapes, to focus on retaining and enhancing the patient's body core temperature during a surgical procedure.

It is a purpose of this invention to fulfill this and other needs in the art in a manner more apparent to the skilled artisan once given the following disclosure.

SUMMARY OF THE INVENTION

In a first embodiment, the present invention pertains to a surgical drape for use in a pre- and/or post-operative environment and in the sterile operating room environment, the surgical drape comprising: a drape panel for covering at least a first portion of a surgical patient during a surgical procedure; a thermal panel adjacent and affixed to the drape panel and overlying the surgical patient; and a heat source affixed to the drape panel.

In another embodiment, the surgical drape for use in a pre- and/or post-operative environment and in the sterile operating room environment comprises: a drape panel for covering at least a first portion of a surgical patient during a surgical procedure; and a heat source comprising at least first air activated chemical warming device and is selectively positioned and affixed to the drape panel. A thermal panel adjacent and affixed to the drape panel is optional.

And in another embodiment, the surgical drape for use in a pre- and/or post-operative environment and in the sterile operating room environment, comprises a drape panel for covering at least a first portion of a surgical patient during a surgical procedure; and a heat source comprising at least first air activated chemical warming device selectively positioned and affixed to the drape panel.

DETAILED DESCRIPTION OF THE DRAWINGS

Provided herein is an inventive surgical drape having a thermal feature and a novel method of using the inventive surgical drape. The thermal feature generally comprises: (1) a thermal layer enabling the patient to retain their own body heat, or (2) a thermal element, in combination with the thermal layer or without a thermal layer. In the variations disclosed herein, the surgical drape assists the patient in retaining body heat without the use of external devices, with wires and tubes, for circulating conditioned air or fluid. The inventive surgical drape also provides an effective barrier to protect a surgical patient and operating room personnel from the transfer of microorganisms, body fluids and particulates that might otherwise cause infections and/or HAIs (hospital Acquired Infections) and potential patient cross-contaminations.

Referring to FIGS. 1-13, various surgical drapes 10 according the present invention are shown to provide an effective barrier to prevent heat loss from a surgical patient, and to protect the surgery patient and operating room personnel from the hazards noted above. The surgical drape 10 includes component parts that work individually and in conjunction with each other each other reduce heat loss in a surgical patient along with providing the protective barrier.

In all embodiments and variations described herein the location of the surgical procedure on the patient and the parts of the patient's body to be kept warm generally determine the size, shape and location of the drape panel 12, thermal panel 14, and/or heat source 18. Intended use of the surgical drape, e.g., use during pre- or post-procedure times or during the surgical procedure, also factors into the specific characteristics and functionality of the surgical drapes 10 shown and described herein. Surgical drape and component dimensions noted in the description below are exemplary and not limiting.

Surgical drapes embodying the present inventive concept offer the following advantages over prior art devices: offers the following advantages: (1) ease of use; (2) improved cost efficiencies; (3) improved time efficiencies; (4) the use of strategically placed thermal material on the drape/patient gown provides the ability of the drape to help maximize body temperature retention throughout surgical procedures; (5) the use of the thermal material on the surgical drape to enhance patient body temperature retention during the surgical pre- and/or post-operative procedures and operating room procedures to ensure infection prevention without compromising quality; and (6) the ability to provide patient thermal material coverage on the patient's body core to retain body temperature thru surgical procedures. Additionally, since no air is being circulated, or machines or tubes needed thus patient cross-contamination issues and concerns are greatly reduced as compared with current surgical drape options.

Figure 1:
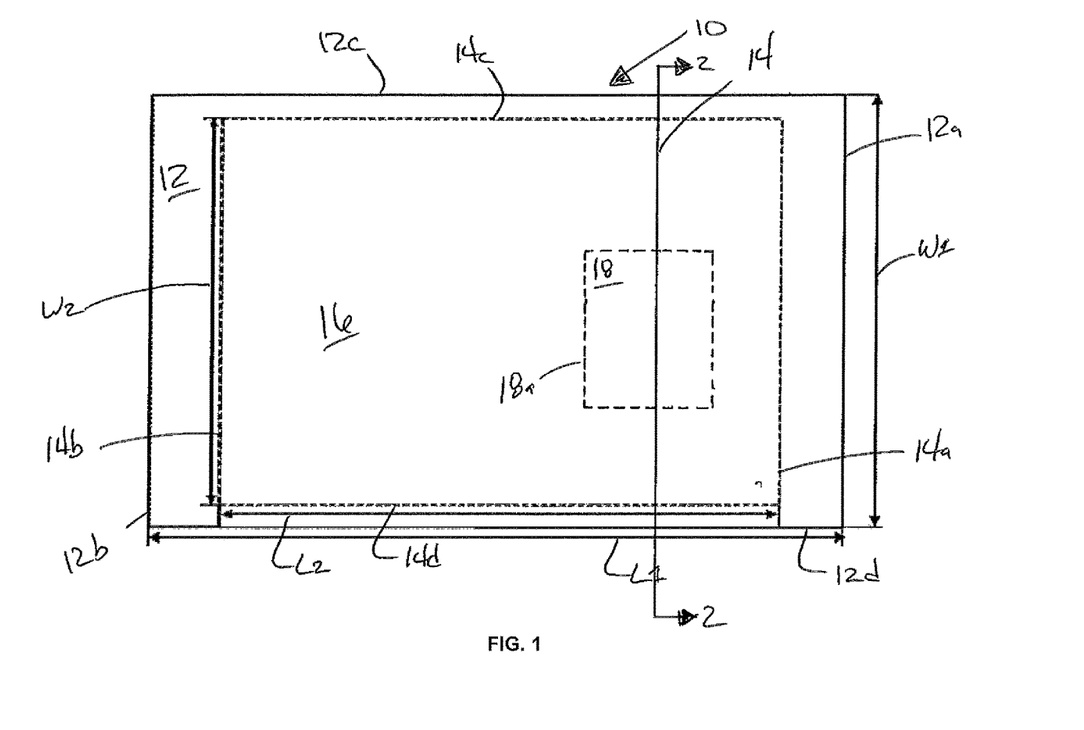
FIG. 1 is a top plan view of a surgical drape in accordance with the present invention.
Figure 2:
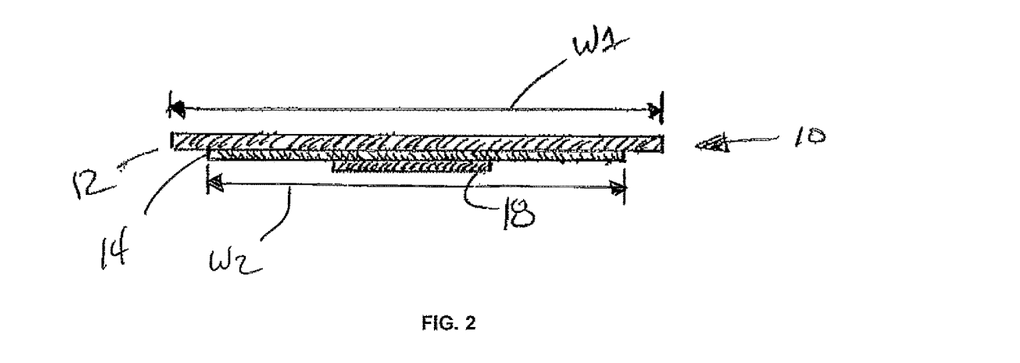
FIG. 2 is a cross-sectional view taken along Section Line 2-2 in FIG. 1.
Figure 3:
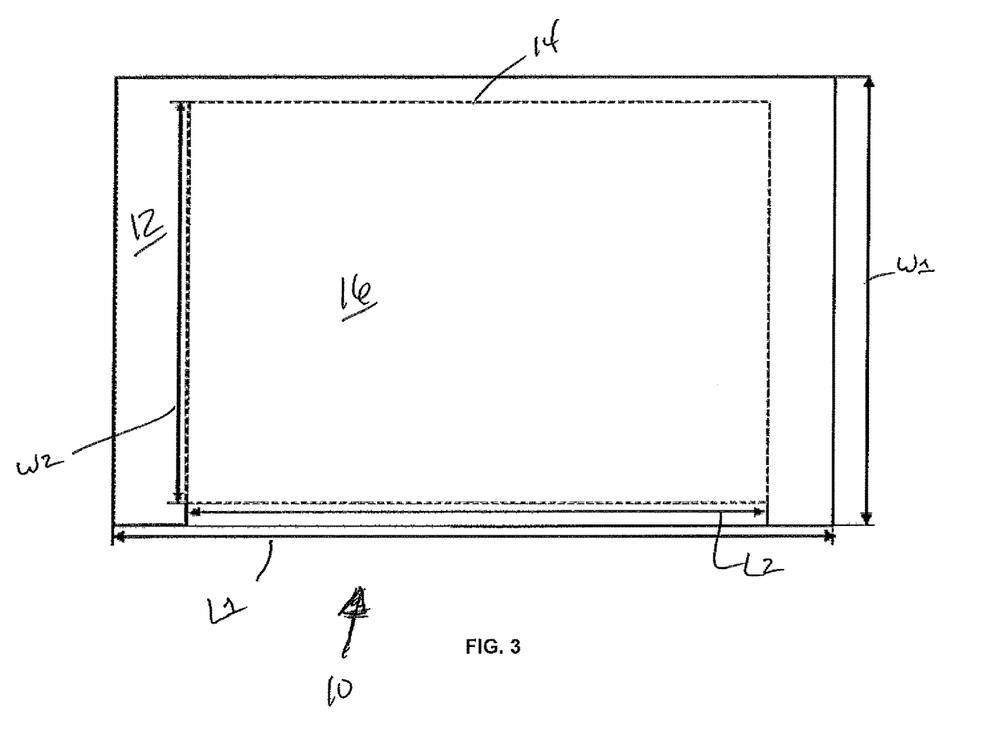
FIG. 3 is top plan view of an alternative version of the surgical drape of FIG. 1.

Turning first to FIGS. 1-3, a surgical drape 10 in accordance with the present invention is shown. The surgical drape 10 comprises a drape panel 12, shown in FIG. 1 as generally rectangular in configuration with opposing pairs of margins or sides 12a, 12b and 12c, 12d. The drape panel 12 is generally dimensioned to cover a surgical patient during a surgical procedure. In operation the surgical drape 10 is positioned on the patient so the drape panel 12 located adjacent to a location where the surgical procedure is to be performed.

Margins 12a, 12b each have a width W1 which in the surgical drape 10 shown in FIG. 1 is approximately 44" and margins 12c, 12d each have a length L1 which in surgical drape 10 shown in FIG. 1 is approximately 76". The drape panel 12 is, preferably, constructed of any suitable lightweight, breathable material (woven or non-woven) that delivers natural comfort to the patient. An example of a suitable material is sold under the product name PROTECT5™ by Welmed, Incorporated. Other suitable surgical drape materials may also be utilized.

A thermal panel 14 is affixed to the underside or bottom surface of the drape panel 12 and is constructed to be contiguous with drape panel 12. The thermal panel 14 defines a first heat retention area 16 on the surgical patient to assist in surgical patient body temperature maintenance. The thermal panel 14 is constructed of any suitable, durable material capable of reflecting the patient's heat back onto the patient. In one embodiment of the invention, the thermal panel 14 is comprised of a heat reflective material. The heat reflective material of the thermal panel 14 is a foil type material.

The thermal panel 14 shown in FIG. 1 is generally rectangular in configuration, having opposing side edges 14a, 14b and 14c, 14d, and is dimensioned substantially similar to drape panel 12. Margins 14a, 14b each have a width W2 which in the surgical drape 10 shown in FIG. 1 is approximately 40" and margins 14c, 14d each have a length L2 which in surgical drape 10 shown in FIG. 1 is approximately 60". The thermal panel 14 is affixed to the drape panel 12 by conventional lamination, adhesive, or gluing techniques. In the surgical drape 10 shown in FIG. 1, the first thermal panel may be composed of a polyester film such as BoPET (Biaxially-oriented polyethylene terephthalate) commonly marketed under the registered trademark MYLAR® and having a thickness range of 0.0005 inches (12 μm) to 0.014 inches (350 μm). Other heat retention materials having similar material and operating characteristics may also be utilized.

In FIGS. 1-2, a heat source 18, secondary to the body heat generated by the surgical patient is affixed to bottom surface drape panel 12 via the first thermal panel 14 and within the heat retention area 16. The heat source 18 can comprise a single thermal element 18a selectively positioned within the heat retention area 16 or a plurality of thermal elements (not shown) selectively positioned within the heat retention area 16. The heat source is selected to provide constant, consistent heat over a desired period of time. The heat source is also selected based on ease of activation and heating time to operational temperature. The type of heat source satisfying these requirements is an air-tight sealed thermal element, where the warming aspect begins when a waterproof/weatherproof seal is removed to expose the internal heating material to oxygen. The heat source is affixed to the drape panel 14 with adhesive or gluing techniques. One such heat source is an air-activated chemical warming device sold under the product name EXOTHERMIX® by Rechargeable Battery Corporation of College Station, Tex. Other heat sources having similar properties and operating characteristics may also be utilized.

Figure 4:
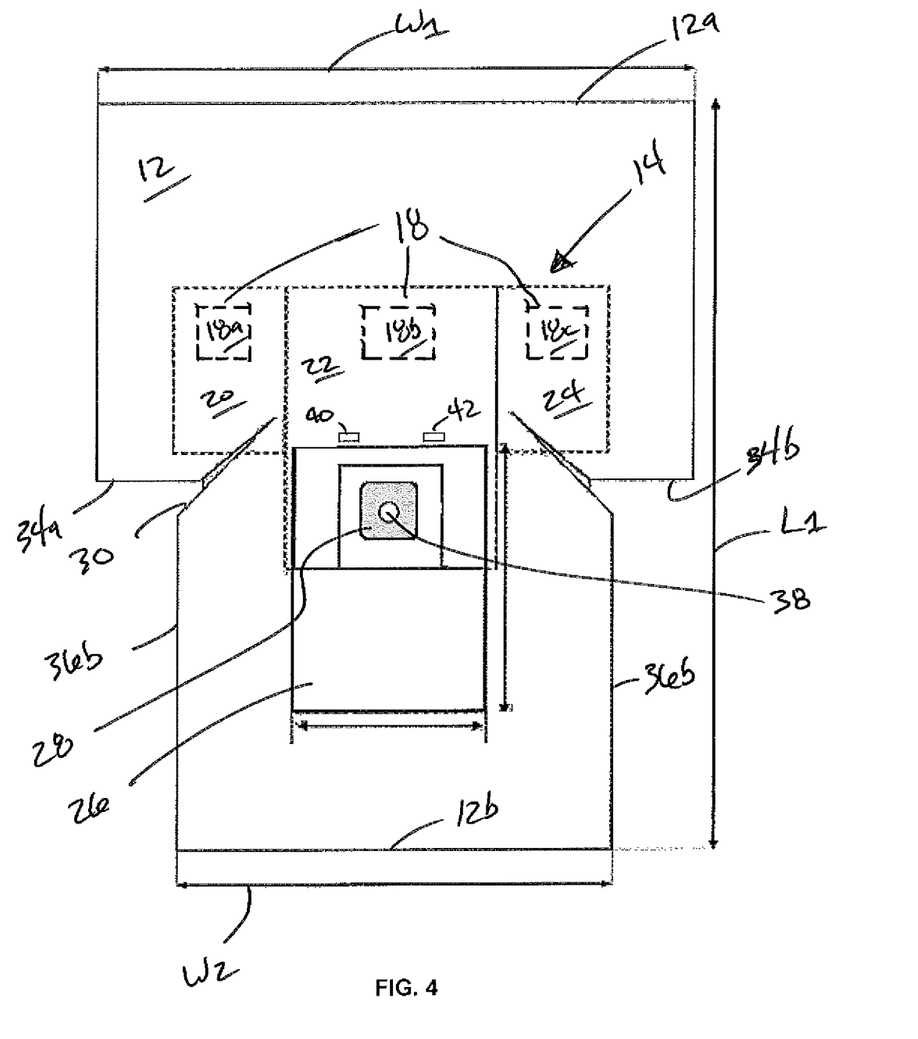
FIG. 4 is a top plan view of a second surgical drape in accordance with the present invention.
Figure 5:
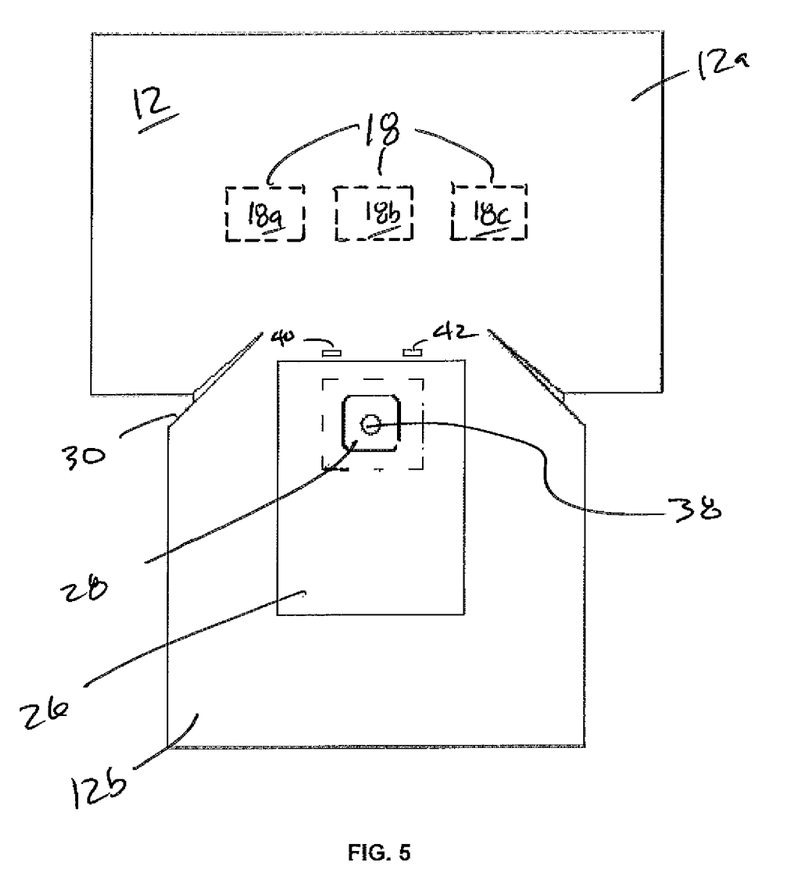
FIG. 5 is top plan view of an alternative version of the surgical drape of FIG. 4.

Additional surgical drapes according to the present invention are shown in FIGS. 4-5. The surgical drape 10 comprises a drape panel 12, a thermal panel 14 (FIG. 4) comprising a first, second, and third segment 20, 22, 24 defining a first heat retention area 16, a heat source 18, and further comprises a reinforcement panel 26, and an incise panel 28. The surgical drape 10 in these figures are constructed to overlay the patient's body, and heat or retain heat in the core of the patient's body during a surgical procedure on the patient's abdominal area.

The drape panel 12 is constructed with sufficient length and width dimensions for covering a surgical patient during a surgical procedure. Exemplary drape panel dimensions for a lower extremity T-shaped surgical drape 10 are approximately 107" at a first width W1 at the top margin 12a of the drape panel 12, approximately 79" at a second width W2 at the bottom margin 12b of the drape panel 12, and an overall length L1 of approximately 133", measured from the top margin 12a to the bottom margin 12b. Material selection considerations for the drape panel 12 of the surgical drape 10 shown in FIGS. 4-5 is the same as for the surgical drape shown in FIG. 1.

The thermal panel 14 in FIG. 4 and its component first, second, and third thermal panel segments 20, 22, 24 are constructed to be contiguous with the drape panel 12 and define a heat retention area 16 over the core of the surgical patient. The thermal panel 14 is preferably constructed from the same material as the thermal panel of the surgical drape shown in FIG. 1 and may be constructed of a single piece of material or a plurality of pieces of material. As seen in FIG. 4, the first, second and third thermal panel segments may be of different size, shape, and/or dimension dependent on the location of the surgical procedure on the patient. The thermal panel 14 is affixed to the bottom surface of the drape panel 12 by conventional means, including lamination, adhesive, or gluing techniques.

Referring to both FIGS. 4-5, the drape panel 12 further includes first and second cut areas 30, 32 that conventionally cut along drape panel 12 at a 45° angle with respect to edges 34a, b and 36a,b of the drape panel 12. The reinforcement panel 26 may be constructed of any suitable polymeric material capable of providing reinforcement around a fenestration 38 in the surgical drape 10. The reinforcement panel 26 is approximately 38"×48" and is attached on the top surface of the drape panel 12 by conventional lamination, adhesive, or gluing. The fenestration 38 is an opening in the surgical drape 10 where the surgical procedure on the patient is to take place.

The incise panel 28 is located within the reinforcement panel 26 affixed to its bottom surface and covers fenestration 38. The incise panel 28, preferably, is constructed of any suitable flexible polymeric material that creates an impervious barrier to the transfer of microorganisms, body fluids and particulates that might otherwise cause infections. Preferably, incise panel 28 is constructed of polyurethane. In the surgical drape shown in FIGS. 4-5, the fenestration 38 is 2.5" diameter conformable circular aperture with surrounding 10"×10" elastic film. The fenestration can also be oval-shape or any other shape suitable for the desired purpose of allowing the patient's arm or leg to be inserted there through. First and second holder 40, 42 are conventional hook and loop tube and cord holders and conventionally attach to the top surface of the drape panel 12 by adhesive tape and/or glue.

Similar to the surgical drape shown in FIG. 1, further aiding in surgical patient body temperature maintenance is a heat source 18, secondary to the body heat generated by the surgical patient, affixed to the surgical drape 10. In FIG. 4, the heat source 18 is affixed to the thermal panel 14 and in FIG. 5 the heat source 18 is affixed directly to the bottom surface of the drape panel 12. The heat source 18 can comprise a single thermal element (not shown) selectively positioned on the drape panel 12 or a plurality of thermal elements 18a, 18b, 18c selectively positioned on the drape panel 12. The heat source 18 may be an air-activated chemical warming device is selected to provide constant, consistent heat over a desired period of time. The heat source is also selected based on ease of activation and heating time to operational temperature. The heat source 18 is affixed to the bottom surface of the drape panel 12 or thermal panel 14 with adhesive, or gluing techniques.

Figure 6:
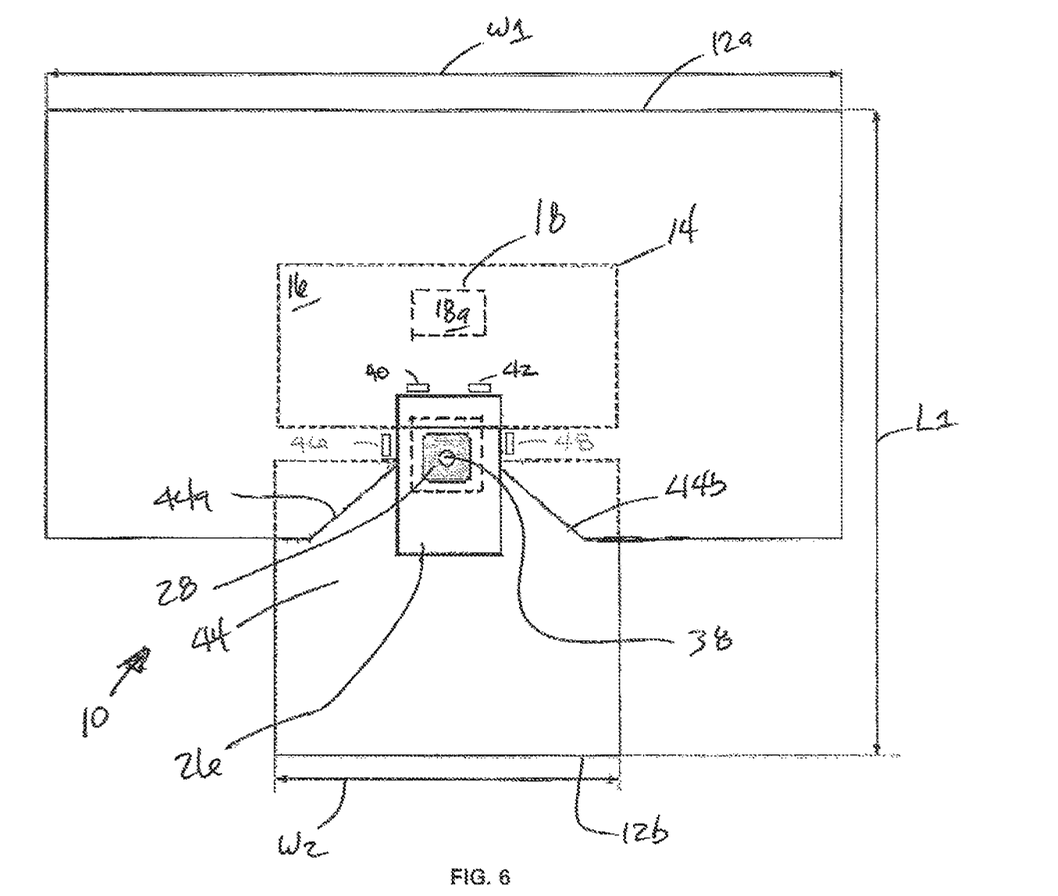
FIG. 6 is a top plan view of a third surgical drape in accordance with the present invention.
Figure 7:
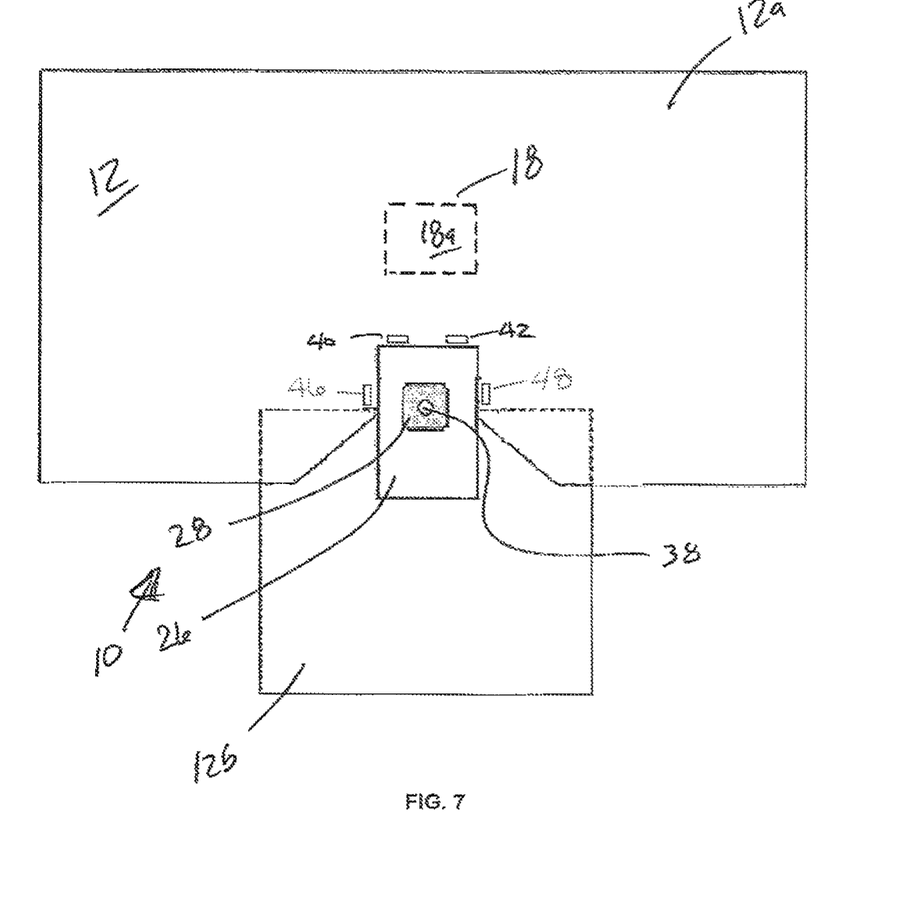
FIG. 7 is a top plan view of an alternative version of the surgical drape of FIG. 6.

Turning to FIGS. 6-7, another surgical drape 10 according to the present invention is shown. The surgical drape 10 comprises a drape panel 12 comprising first and second drape panel segments 12a, 12b, a thermal panel 14 (FIG. 6) defining a first heat retention area 16, a heat source 18, and further comprises a reinforcement panel 26, and an incise panel 28. The surgical drape 10 shown in these figures is constructed to overlay the chest and abdomen area of the patient (the core of the patient's body) during a surgical procedure on the patient's chest and abdominal areas.

The drape panel 12 is comprised of first and second segments 12a, 12b, with the first segment 12a overlying the second segment 12b to form a t-shape surgical drape 10. To reduce material quantity, the first segment 12a include a cut-out portion 44 defined by first, second, and third edges 44a, 44b, (not shown). The drape panel 12 is constructed with sufficient length and width dimensions for covering a surgical patient during a surgical procedure. Exemplary drape panel dimensions for a lower extremity T-shaped surgical drape 10 are approximately 142" at a first width W1 at the top margin 12a of the drape panel 12, approximately 61" at a second width W2 at the bottom margin 12b of the drape panel 12, and an overall length L1 of approximately 115", measured from the top margin 12a to the bottom margin 12b. Material selection considerations for the drape panel 12 of the surgical drape 10 shown in these figures is the same as for the surgical drape shown in the previous figures.

The thermal panel 14 in FIG. 6 is affixed to the underside or bottom surface of the drape panel 12 and is constructed to be contiguous with drape panel 12. The thermal panel 14 defines a first heat retention area 16 on the surgical patient to assist in surgical patient body temperature maintenance. Similar to the surgical drapes shown in the previous figures, the thermal panel 14 is constructed of any suitable, durable material capable of reflecting the patient's heat back onto the patient and is preferably constructed from the same material as the thermal panel of the surgical drapes shown in the previous figures. The thermal panel 14 is affixed to the bottom surface of the drape panel 12 by conventional lamination, adhesive, or gluing techniques.

Turning to FIGS. 6-7, the reinforcement panel 26 may be constructed of any suitable polymeric material capable of providing reinforcement around a fenestration 38 in the surgical drape 10. The reinforcement panel 26 is approximately 20"×34" and is attached on the top surface of the drape panel 12 by conventional lamination, adhesive, or gluing. The fenestration 38 is an opening in the surgical drape 10 where the surgical procedure on the patient is to take place.

The incise panel 28 is located within the reinforcement panel 26 affixed to its bottom surface and covers fenestration 38. The incise panel 28, preferably, is constructed of any suitable flexible polymeric material that creates an impervious barrier to the transfer of microorganisms, body fluids and particulates that might otherwise cause infections. Preferably, incise panel 28 is constructed of polyurethane. In the surgical drape of these figures, the fenestration 38 is a conformable circular aperture with surrounding 8"×8" elastic film. The fenestration can also be oval-shape or any other shape suitable for the desired purpose of allowing the patient's arm or leg to be inserted there through. A plurality of holders 40, 42, 46, 48. The plurality of holders 40, 42, 46, 48 are conventional hook and loop tube and cord holders and conventionally attach to the top surface of the drape panel 12 by adhesive tape and/or glue.

Similar to the surgical drape shown in the previous figures, aiding in surgical patient body temperature maintenance is heat source 18 affixed to the surgical drape 10 within the heat retention area 16. In FIG. 6, the heat source 18 is affixed to the thermal panel 14 within the heat retention area 16 and in FIG. 7 the heat source is affixed to the bottom surface of the drape panel 12. The heat source 18 can comprise a single thermal element (not shown) selectively positioned on the drape panel 12 or a plurality of thermal elements 18a, 18b, 18c selectively positioned on the drape panel 12. The heat source 18 may be an air-activated chemical warming device is selected to provide constant, consistent heat over a desired period of time. The heat source is also selected based on ease of activation and heating time to operational temperature. The heat source 18 is affixed to the surgical drape 10 with adhesive, or gluing techniques.

Figure 8:
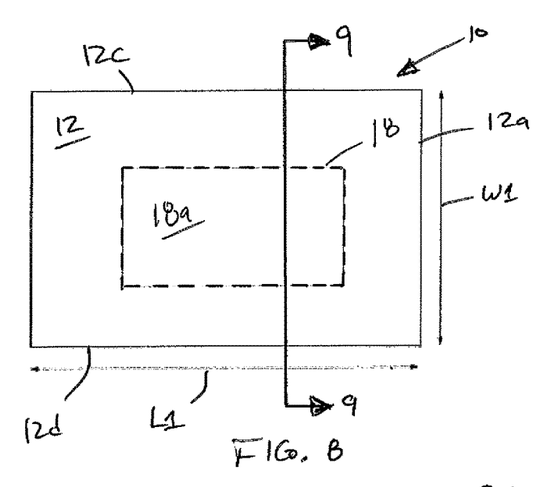
FIG. 8 is a top plan view of a fourth surgical drape in accordance with the present invention.
Figure 9:
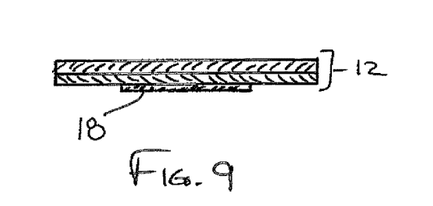
FIG. 9 is a cross-sectional view taken along Section Line 9-9 in FIG. 8.

Turning now to FIGS. 8-11, additional embodiments and variations of the inventive surgical drape are shown. Referring first to FIGS. 8-9, a surgical drape 10 configured as a core thermal drape is shown. The core thermal surgical drape 10 is dimensioned for use on the upper body of the patient to focus on main core temperature maintenance. This surgical drape is intended for use while the patient is waiting for surgery, during the procedure, and/or after the procedure. As with other embodiments described herein, the surgical drape 10 comprises a drape panel 12, shown in FIGS. 8-9 is generally rectangular in configuration with opposing pairs of margins or sides 12a, 12b and 12c, 12d.

Margins 12a, 12b each have a width W1 which in the surgical drape 10 shown in FIG. 8 is approximately 14" and margins 12c, 12d each have a length L1 which in surgical drape 10 shown in FIG. 8 is approximately 26". The drape panel 12 is preferably, is constructed of any suitable lightweight, breathable material that delivers natural comfort and protection to the patient. The drape panel 12 is preferably, is constructed of any suitable lightweight, breathable material (woven or non-woven) that delivers natural comfort to the patient. An example of a suitable material is sold under the product name PROTECT5™ by Welmed, Incorporated. Other suitable surgical drape materials may also be utilized. A bottom layer comprises an adhesive layer to hold the surgical drape 10 onto the patient or another drape.

Aiding in surgical patient body temperature maintenance is heat source 18, affixed to the top surface of the drape panel 12. The heat source 18 can comprise a single thermal element 18a or a plurality of thermal elements (not shown) selectively positioned on the drape panel 12. The heat source is selected to provide constant, consistent heat over a desired period of time. The heat source is also selected based on ease of activation and heating time to operational temperature. The heat source is affixed to the drape panel 14 with adhesive, or gluing techniques. One such heat source an air-activated chemical warming device sold under the product name EXOTHERMIX® by Rechargeable Battery Corporation of College Station, Tex.

Figure 10:
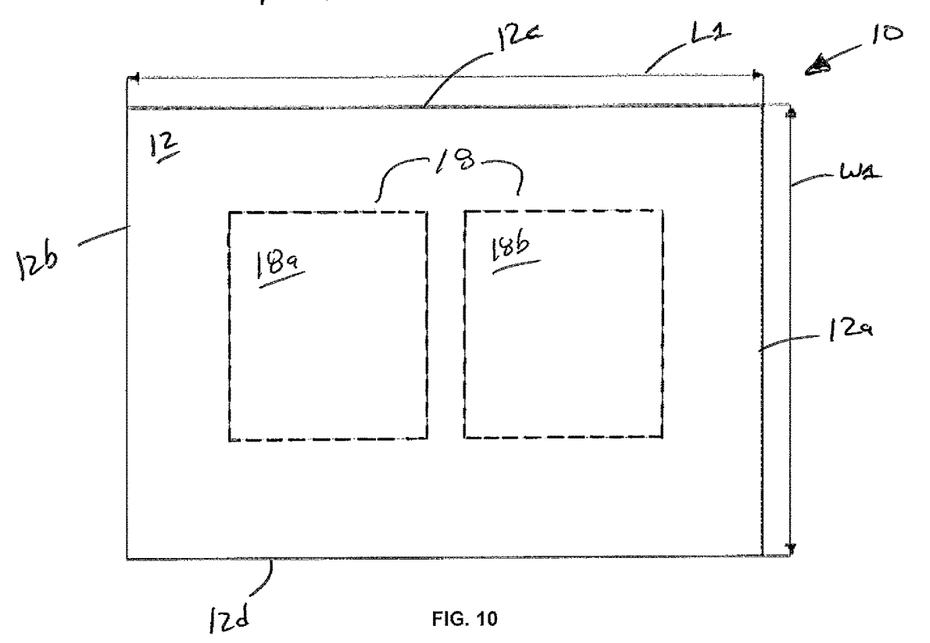
FIG. 10 is a top plan view of a fifth surgical drape in accordance with the present invention.

Referring to FIG. 10, a surgical drape 10 configured as a body thermal drape is shown. The body thermal surgical drape 10 is dimensioned for use across the entire upper body of the patient or, turned lengthwise, can cover the patient from upper body to lower/mid body. This surgical drape is intended for use while the patient is waiting for surgery, during the procedure, and/or after the procedure. The surgical drape 10 shown in these figures is similar to in configuration to the surgical drape shown in FIGS. 8-9. Margins 12a, 12b each have a width W1 which is approximately 44" and margins 12c, 12d each have a length L1 which is approximately 60". The heat source 18 comprise a plurality of thermal elements 18a, 18b selectively positioned on the drape panel 12.

Figure 11:
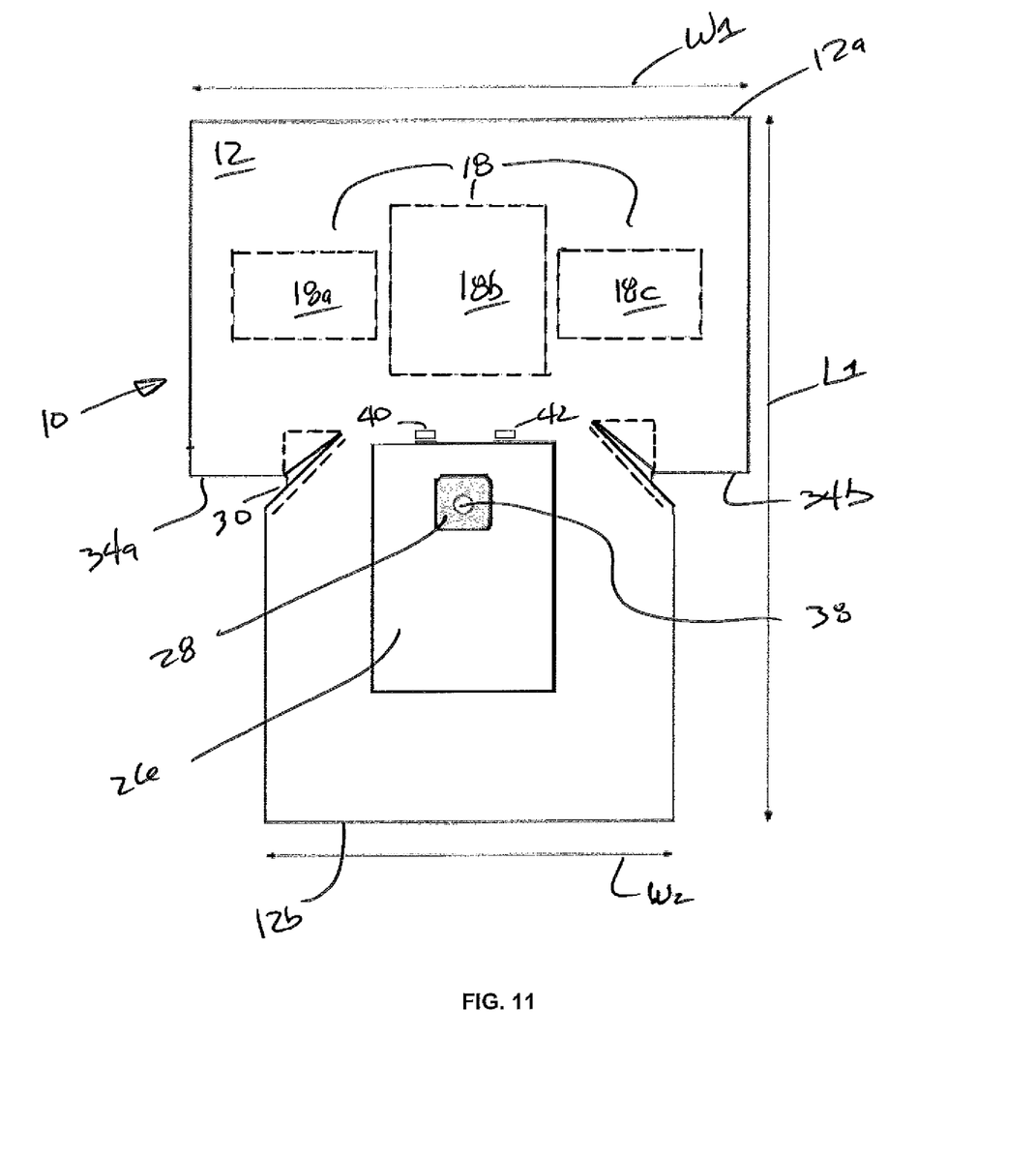
FIG. 11 is a top plan view of a sixth surgical drape in accordance with the present invention.

FIG. 11, shows a lower extremity surgical drape 10 according to the present invention. The surgical drape 10 comprises a drape panel 12, and a heat source comprising a plurality of thermal elements 18a, 18b, 18c disposed on the top surface of the drape panel 12, and further comprises a reinforcement panel 26, and an incise panel 28. The surgical drape 10 shown in FIG. 11 is constructed to overlay the chest and abdomen area of the patient (the core of the patient's body) during a surgical procedure on a lower extremity of the patient.

The drape panel 12 is constructed with sufficient length and width dimensions for covering a surgical patient during a surgical procedure. Exemplary drape panel dimensions for a lower extremity T-shaped surgical drape 10 are approximately 107" at a first width W1 at the top margin 12a of the drape panel 12, approximately 79" at a second width W2 at the bottom margin 12b of the drape panel 12, and an overall length L1 of approximately 133", measured from the top margin 12a to the bottom margin 12b. Material selection considerations for the drape panel 12 of the surgical drape 10 in this figure is similar to the other embodiments and variations of the invention described herein. The heat source 18 may be an air-activated chemical warming device is selected to provide constant, consistent heat over a desired period of time. The heat source is also selected based on ease of activation and heating time to operational temperature. The heat source 18 is affixed to the drape panel 14 with adhesive, or gluing techniques. Individual thermal elements 18a, 18b, 18c of the heat source 18 may be of different size, shape, and/or orientation dependent on the location of the surgical procedure on the patient and are affixed to the top surface of the drape panel 12. The center thermal element 18b overlies the chest of the patient and the side thermal elements 18a, 18c overlie the shoulders and arms of the patient.

The drape panel 12 further includes first and second cut areas 30, 32 that conventionally cut along drape panel 12 at a 45° angle with respect to edges 34ab and 36a,b of the drape panel 12. The reinforcement panel 26 may be constructed of any suitable polymeric material capable of providing reinforcement around a fenestration 38 in the surgical drape 10. The reinforcement panel 26 is approximately 38"×48" in the surgical drape of FIG. 9 and is attached on the top surface of the drape panel 12 by conventional lamination, adhesive, or gluing. The fenestration 38 is an opening in the surgical drape 10 where the surgical procedure on the patient is to take place.

The incise panel 28 is located within the reinforcement panel 26 affixed to its bottom surface and covers fenestration 38. The incise panel 28, preferably, is constructed of any suitable flexible polymeric material that creates an impervious barrier to the transfer of microorganisms, body fluids and particulates that might otherwise cause infections. Preferably, incise panel 28 is constructed of polyurethane. In the surgical drape shown in FIG. 11, the fenestration 38 is 2.5" diameter conformable circular aperture with surrounding 10"×10" elastic film. The fenestration can also be oval-shape or any other shape suitable for the desired purpose of allowing the patient's arm or leg to be inserted there through. First and second holder 40, 42 are conventional hook and loop tube and cord holders and conventionally attach to the top surface of the drape panel 12 by adhesive tape and/or glue.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A surgical drape for use in a sterile environment, the surgical drape configured to cover a body portion of a surgical patient, the surgical drape comprising:
    a drape panel adapted to cover the body portion of the surgical patient;
    a thermal panel affixed to the drape panel and overlying the body portion; and
    a plurality of thermal elements independently formed from the drape panel and the thermal panel, and each thermal element affixed to the thermal panel,
    wherein each thermal element in the plurality of thermal elements is affixed only the thermal panel and free from affixation to the drape panel.

2. The surgical drape of claim 1 wherein the thermal panel defines a heat retention area.

3. The surgical drape of claim 1 wherein the plurality of thermal elements are adapted to be selectively positioned and affixed to the thermal panel during preparation of the surgical drape for use.

4. The surgical drape of claim 1 wherein the plurality of thermal elements includes at least a first air-activated chemical warming device.

5. The surgical drape of claim 1 wherein the thermal panel comprises a plurality of independently formed segments.

6. The surgical drape of claim 5 wherein at least one of the plurality of thermal panel segments is a different shape or size than the other thermal panel segments.

7. The surgical drape of claim 1 wherein the thermal panel is comprised of a heat reflective material.

8. The surgical drape of claim 7 wherein the heat reflective material of the thermal panel is a foil type material.

9. A surgical drape for use in a sterile environment, the surgical drape configured to cover a body portion of a surgical patient, the surgical drape comprising:
    a drape panel adapted to cover the body portion of the surgical patient;
    a thermal panel comprising a foil type, heat reflective material affixed to a bottom surface of the drape panel and defining a heat retention area adapted to overlie the body portion; and
    an active heat source comprising a plurality of thermal elements independently formed from the drape panel and the thermal panel, and each thermal element affixed to the thermal panel,
    wherein each of the plurality of thermal elements is affixed only the thermal panel and free from affixation to the drape panel.

10. The surgical drape of claim 9 wherein the plurality of thermal elements are adapted to be selectively positioned and affixed to the thermal panel during preparation of the surgical drape for use.

\* \* \* \* \*